(12) United States Patent
Weinberger et al.

(10) Patent No.: US 10,793,816 B2
(45) Date of Patent: Oct. 6, 2020

(54) TISSUE CULTURE CHIP

(71) Applicant: Augusta University Research Institute, Inc., Atlanta, GA (US)

(72) Inventors: Paul M. Weinberger, Augusta, GA (US); Frederick A. Rueggeberg, Augusta, GA (US); Donald J. Mettenburg, Evans, GA (US); Tanner Mobley, Jacksonville, FL (US)

(73) Assignee: AUGUSTA UNIVERSITY RESEARCH INSTITUTE, INC., Augusta, GA (US)

( * ) Notice: Subject to any disclaimer, the term of this patent is extended or adjusted under 35 U.S.C. 154(b) by 1122 days.

(21) Appl. No.: 14/472,683

(22) Filed: Aug. 29, 2014

(65) Prior Publication Data

US 2015/0065588 A1 Mar. 5, 2015

Related U.S. Application Data

(60) Provisional application No. 61/872,221, filed on Aug. 30, 2013.

(51) Int. Cl.
*C12M 3/00* (2006.01)
*C12M 1/12* (2006.01)
*G01N 33/50* (2006.01)

(52) U.S. Cl.
CPC ............ *C12M 23/42* (2013.01); *C12M 23/04* (2013.01); *C12M 25/14* (2013.01); *G01N 33/5011* (2013.01)

(58) Field of Classification Search
CPC .......... C12N 1/20; C12M 23/08; C12M 27/20
See application file for complete search history.

(56) References Cited

U.S. PATENT DOCUMENTS

| 6,060,306 A * | 5/2000 | Flatt ...................... A61F 2/0095 |
| | | 435/286.5 |
| 7,416,884 B2 * | 8/2008 | Gemmiti ................ C12M 25/14 |
| | | 435/293.1 |
| 2007/0042490 A1 * | 2/2007 | Welter ................... C12M 23/24 |
| | | 435/325 |

OTHER PUBLICATIONS

Carletti, et al., "Scaffolds for tissue engineering and 3D cell culture", Methods Mol Biol., 695:17-39 (2011).
Go, et al., "Both epithelial cells and mesenchymal stem cell-derived chondrocytes contribute to the survival of tissue-engineered airway transplants in pigs", J Thorac Cardiovasc Surg., 139:437-443 (2010).

(Continued)

*Primary Examiner* — William H. Beisner
*Assistant Examiner* — Danielle B Henkel
(74) *Attorney, Agent, or Firm* — Smith, Gambrell & Russell, LLP (57) ABSTRACT

A dual chamber bioreactor for producing complex, multi-layer tissue, organs, organ parts, and skin replacements has been developed. The bioreactor is modular and incorporates a removable tissue culture cassette. By rotating the dual chamber bioreactor along the horizontal axis, different populations of cells with different growth requirements can be cultured on the different surfaces of the tissue culture cassette that are exposed to different media reservoirs. Culturing different populations of cells on different surfaces of the tissue culture cassette enables the production of multilayer tissue and organs. The tissue culture cassette can contain one or more discrete tissue culture sections.

20 Claims, 9 Drawing Sheets

(56) References Cited

OTHER PUBLICATIONS

Liu and Karasek, "Isolation and Growth of Adult Human Epidermal Keratinocytes in Cell Culture", J Inv Derm 71(2):157-64 (1978).
McLaughlin-Drubin and Meyers, "Propagation of infectious, high-risk HPV in organotypic "raft" culture", Methods Mol Med., 119:171-86 (2005).
Shimizu, et al, Polysurgery of cell sheet grafts overcomes diffusion limits to produce thick, vascularized myocardial tissues\, FASEB J, 20:708-10 (2006).

\* cited by examiner

TISSUE CULTURE CHIP

CROSS REFERENCE TO RELATED APPLICATIONS

This application claims benefit to U.S. Ser. No. 61/872,221 filed on Aug. 30, 2013, and which is incorporated by reference in its entirety.

FIELD OF THE INVENTION

The invention is generally directed to tissue culture methods and systems.

BACKGROUND OF THE INVENTION

Progress in regenerative medicine is developing at an incredible pace. Scientists are now using tissue engineering techniques to restore liver function in mice, to regrow human muscle, and even to implant bioengineered blood vessels into ailing patients. Much of this progress has been focused on the goal of growing complete organs in the laboratory. For example, U.S. Pat. No. 8,478,437 to Boyden, et al. describes using 3-D printing to produce blood vessel sleeves. Despite these advances, organogenesis still has significant obstacles to overcome.

A significant obstacle for organogenesis performed on flat surfaces such as culture flasks is the oxygen diffusion limitation. Tissue contains multiple layers, and as the tissue grows, new layers are added. The addition of the new layers limits the access of the first layers to nutrients and importantly, to oxygen. The body addresses this limited access by producing blood vessels to deliver oxygen and nutrients to all layers of tissue. In tissue culture, it is very difficult to grow multiple layered tissue because the engineered tissue does not grow blood vessels. In cell sheet engineering, thicker and high cell-dense 3D tissues without blood vessels are reported to be unable to survive in vivo (Shimizu, T., et al., FASEB J, 20:708-710 (2006)).

Growing an organ or complex tissue in culture often requires seeding different cell types onto different surfaces of a matrix or scaffold. These different cell types can require different nutrients and growth factors to form different layers of the organ. Additionally, the different layers of the tissue culture may require different physical forces to grow specialized cells.

Therefore, it is an object of the invention to provide systems and methods for producing multiple layered tissue or an organ.

It is another object of the invention to provide a bioreactor configured to provide different nutrients and physical forces to different layers of tissue culture matrix or scaffold.

It is another object of the invention to provide systems and methods for high-through-put drug screening on tissue.

SUMMARY OF THE INVENTION

A bioreactor for producing complex, multilayer tissue, organs, organ parts, and skin replacements has been developed. In one embodiment, the bioreactor is dual chamber bioreactor. The bioreactor can be modular and includes a removable tissue culture cassette, two media reservoirs, and receiver block. By rotating the dual chamber bioreactor along the horizontal axis, different populations of cells with different growth requirements can be cultured on the different surfaces of the tissue culture cassette that are exposed to different media reservoirs, shear forces, and air. Culturing different populations of cells on different surfaces of the tissue culture cassette enables the production of multilayer tissue and organs. The tissue culture cassette can contain one or more discrete tissue culture sections. In one embodiment the tissue culture cassette is removable from the bioreactor.

An exemplary tissue culture cassette contains a first and second gasket, wherein the first and second gaskets each contain an opening that aligns with the opening of the other gasket when the first and second gaskets are combined. A cell culture matrix or scaffold is sandwiched between the first and second gasket and covers the aligned openings of the gaskets to form a tissue culture cassette that provides a diffusion barrier between the two media reservoirs when the bioreactor is assembled. The diffusion barrier is effective for preventing or inhibiting diffusion of water and several biological molecules such as albumin, dextran, and IgG between the two media reservoirs. In one embodiment, the tissue culture cassette contains a first gasket that has projections on it that are matingly received by the second gasket to form the tissue culture cassette.

The tissue culture cassette is generally configured to align the openings in the gaskets covered by the cell culture matrix or scaffold with corresponding openings in the dual chambers also referred to as first and second media reservoirs. By aligning the covered openings of the gaskets with the openings of the first and second media reservoirs, a diffusion barrier between the openings of the first and second media reservoirs is formed. In a preferred embodiment, the tissue culture matrix or scaffold contains decellularized tissue, such as decellularized trachea.

The gaskets can be made of polyvinyl siloxane and can have a plurality of openings covered by the cell culture matrix or scaffold for use in high through put screening. For example, the gaskets can have at least 10 to 100 openings. The media reservoirs would have a corresponding number of openings in corresponding positions so that the openings in the media reservoirs align with the openings in the gaskets when the bioreactor is assembled.

Another embodiment provides a bioreactor having a first and second media reservoir, wherein the first and second media reservoir have at least one opening on a cell culture surface of the reservoir, wherein the first and second reservoirs are positioned so that the cell culture surfaces containing the opening of each reservoir face each other and the opening of each reservoir aligns with the opening of the other reservoir. The bioreactor also contains a tissue culture cassette having a first and second gasket, wherein the first and second gaskets each have an opening that aligns when the first and second gaskets are combined. The tissue cassette has a cell culture matrix or scaffold sandwiched between the first and second gasket that covers the aligned openings of the gaskets to form a diffusion barrier. The tissue culture cassette is also positioned between the first and second media reservoirs so that the covered openings in the first and second gaskets align with the openings in the cell culture surfaces of the first and second media reservoirs to form a diffusion barrier between the first and second media reservoirs. The bioreactor also has a means for applying sufficient pressure on the media reservoirs to produce a seal between the media reservoirs and the tissue culture cassette to prevent media leakage out of the openings in the cell culture surface of the media reservoirs. The means for applying pressure can be a receiver Hock optionally containing elastomeric bands. In certain embodiments a sealant can be used to prevent or inhibit media leakage from between the tissue culture cassette and the media reservoirs.

Suitable sealants are known in the art and include but are not limited to organic sealants, oil or grease based sealants, glues or adhesives.

Methods of using the bioreactor are also provided. The methods include using the bioreactor in single experiment tissue engineering, skin graft production, dermatology drug testing, production of skin sheets, skin cancer testing, production of mucosal sheets, viral particle production, and high-throughput screening of drugs.

BRIEF DESCRIPTION OF THE DRAWINGS

FIGS. 11A and 11B are another embodiment of the gaskets that can be used to form a tissue culture cassette.

DETAILED DESCRIPTION OF THE INVENTION

I. Tissue Culture Bioreactor

Rotating bioreactors are provided that can be used to grow complex tissue constructs containing at least two different types of cells, organs, sections of organs, multilayered replacement skin segments, grafts, and stem cells, for transplantation into a subject, preferably a human subject. The rotating bioreactors are modular and contain a first and second media reservoir. Each reservoir has one or more openings in the bottom of the reservoir as well as a port for receiving or removing media into or out of the reservoir. The bottom is typically a planar surface for culturing cells, tissue or organs. The openings in the reservoirs are positioned so that they align when the bottoms of the media reservoirs are paired together. A tissue culture matrix or scaffold sandwiched between two gaskets (referred to as a "tissue chip") covers each opening and creates a diffusion barrier that separates the media reservoirs from each other. In one embodiment, the media reservoirs are held together with a receiver block 54. Clamps, bands, or cables can be placed around the receiver block to compress the components of the bioreactor together to inhibit or reduce leakage of media out of the media reservoirs and into the environment. In certain embodiments, the media from the media reservoirs can diffuse through the openings in the gaskets and enter the other media reservoir. The media reservoirs are clamped together to produce a mechanical, watertight seat between the media reservoirs and the tissue chip to prevent leakage of media from the reservoirs. In some embodiments, a sealant is used between the tissue culture cassette and the media reservoirs to inhibit or reduce leakage of media into the environment. The sealant can be a grease, oil, adhesive, synthetic polymer, organic polymer, glue or a combination thereof. The assembled rotating bioreactor 10 is coupled to a motor to rotate the bioreactor around the horizontal axis. An exemplary motor assembly is described in U.S. Ser. No. 61/794,938 which is incorporated by reference in its entirety.

A. Media Reservoirs

Figure 1:
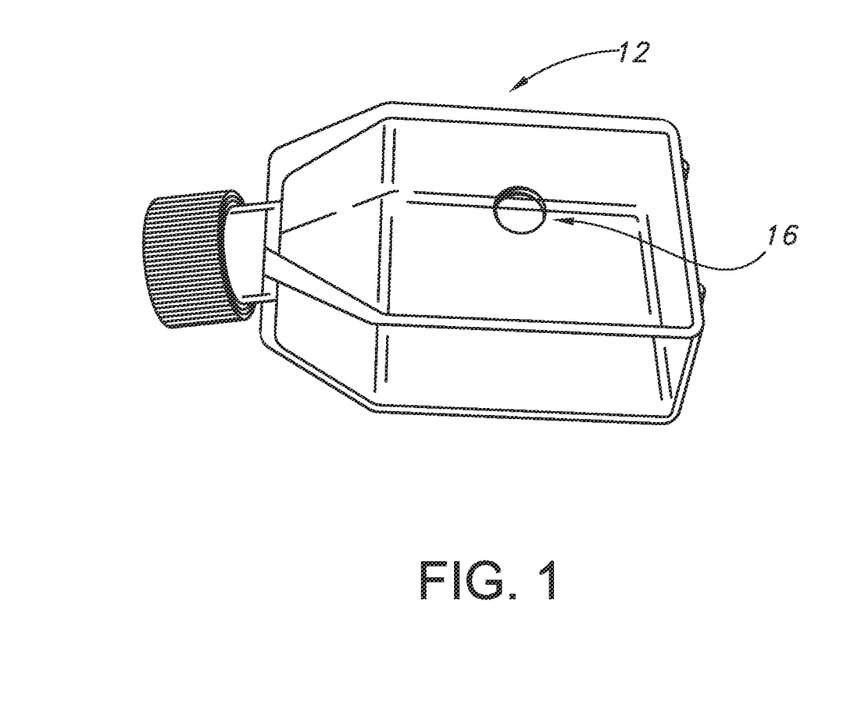
FIG. 1 shows a tissue culture flask functioning as a media reservoir 12.

The media reservoirs 12 can be standard tissue culture flasks as shown in FIG. 1, modified to contain at least one opening 16. The opening 16 is on the bottom of the culture flask 12. The bottom of the culture flask is typically the cell culture surface of the flask. Media reservoirs can be made of a material that enables microscopic or electromagnetic monitoring of the culture media or cells cultured in the media reservoir. Exemplary media reservoirs include, but are not limited to those available from VWR and can be straight-neck or canted-neck flasks with a plug-seal cap for use in open or closed incubation. Some can have a rigid, phenolic lined cap that spins on. Suitable flasks are sterilized by gamma irradiation and are nonpyrogenic.

In certain embodiments, the opening or openings 16 in the media reservoirs 12 can be of any geometry, but are preferably circular. The bioreactors can have 1, 2, 3, 4, 5, 6, 7, 8, 9, 10, 20, 30, 40, 50, 60, 70, 80, 90, or 100 openings, each covered with an individual tissue chip. Alternatively, a single tissue chip with 1, 2, 3, 4, 5, 6, 7, 8, 9, 10, 20, 30, 40, 50, 60, 70, 80, 90, or 100 openings, each covered with individual tissue culture matrix or scaffold can be used. In one embodiment, the tissue chip has 1, 2, 3, 6, 9, 16, 24, 96 openings.

B. Cells to Culture

Different types of cells and different combinations of cells can be cultured on different sides of the tissue chip to produce multilayer tissue constructs. Each media reservoir can contain media specific for the type of cells seeded on tissue chip in fluid communication with the media reservoir. Fibroblasts, keratinocytes, endothelial cells, chondrocytes, stem cells, induced phiripotent stem cells, embryonic stem cells, adult stem cells, mesenchymal stem cells, or combinations and subcombinations thereof can be seeded on the scaffold or matrix in the tissue chip. The two sides of scaffold or matrix of the tissue chip can be seeded with cells of differing cell lineages or combinations of cell lineages. Cell lineages include mesynchymai, endothelial, or ectodermal cell lineages. The cells can be allogenic. In other embodiments, the cells seeded on the constructed are genetically modified, for example to express a heterologous gene, or to overexpress an endogenous gene.

C. Tissue Culture Chip

Figure 2A:
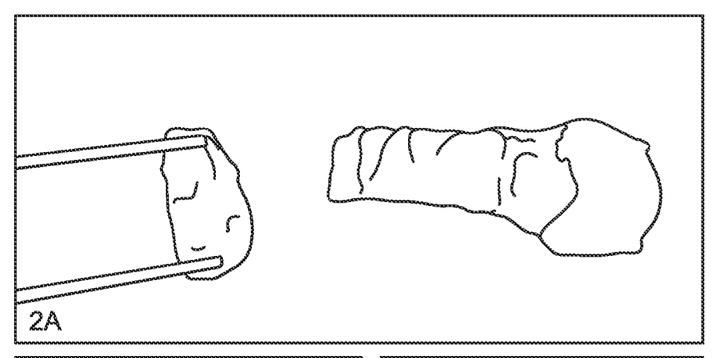
FIG. 2A shows decellularized trachea.
Figure 2B:
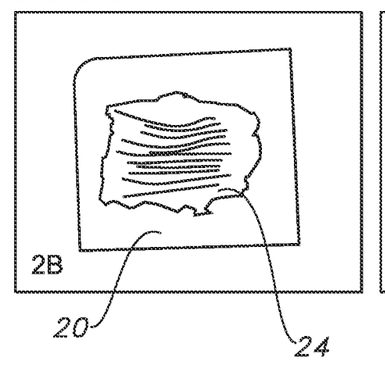
FIG. 2B shows gasket 20 with decellularized trachea 24 covering an opening in gasket 20.
Figure 2C:
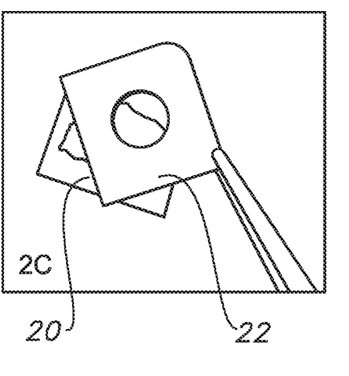
FIG. 2C shows the disassembled components of a tissue culture cassette or "tissue chip".
Figure 5:
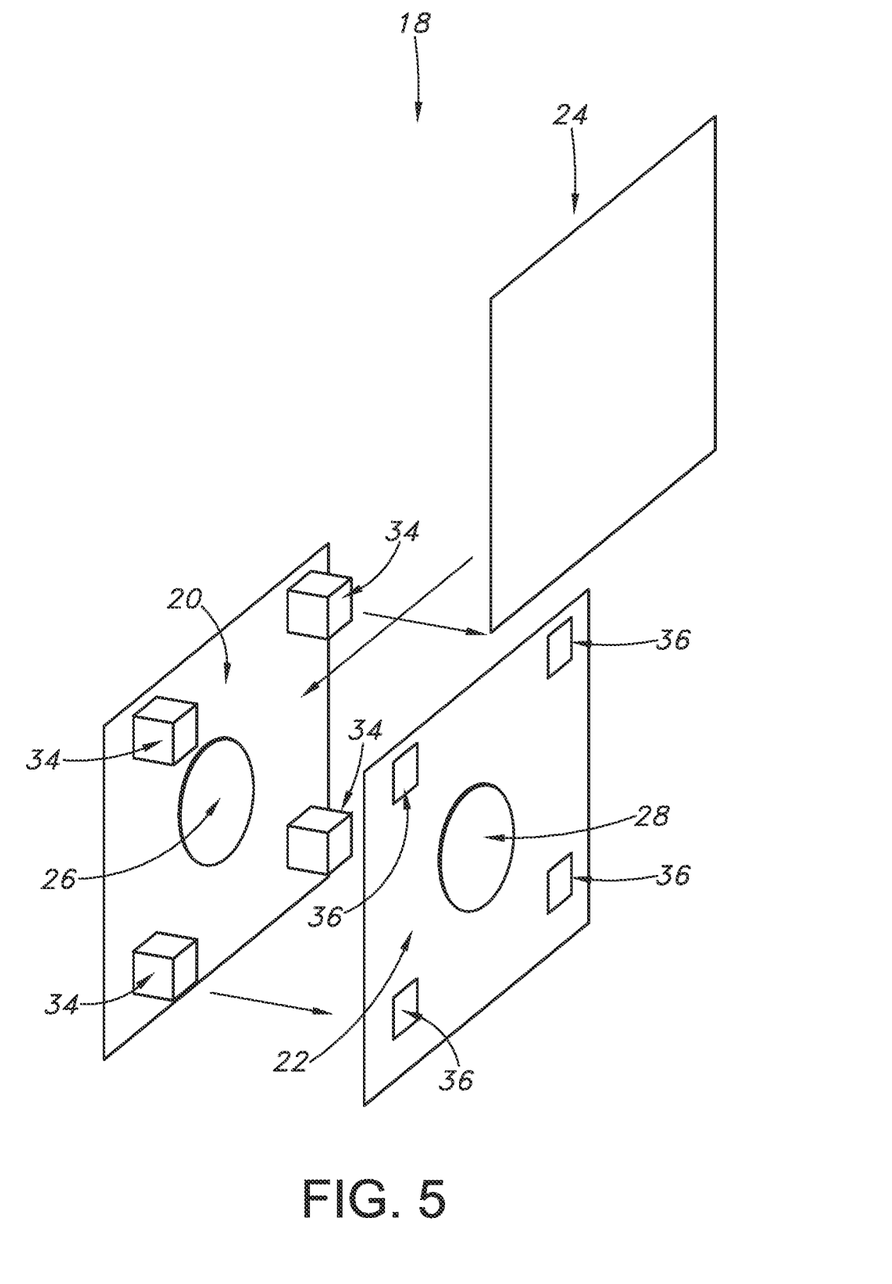
FIG. 5 is an exploded schematic of an exemplary tissue cassette 18.
Figure 6:
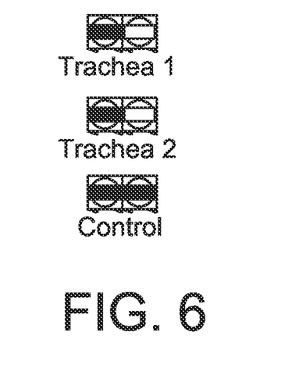
FIG. 6 is a photograph showing that decellularized trachea does not allow diffusion of fluorescently tagged dextran relative to a control.
Figure 7:
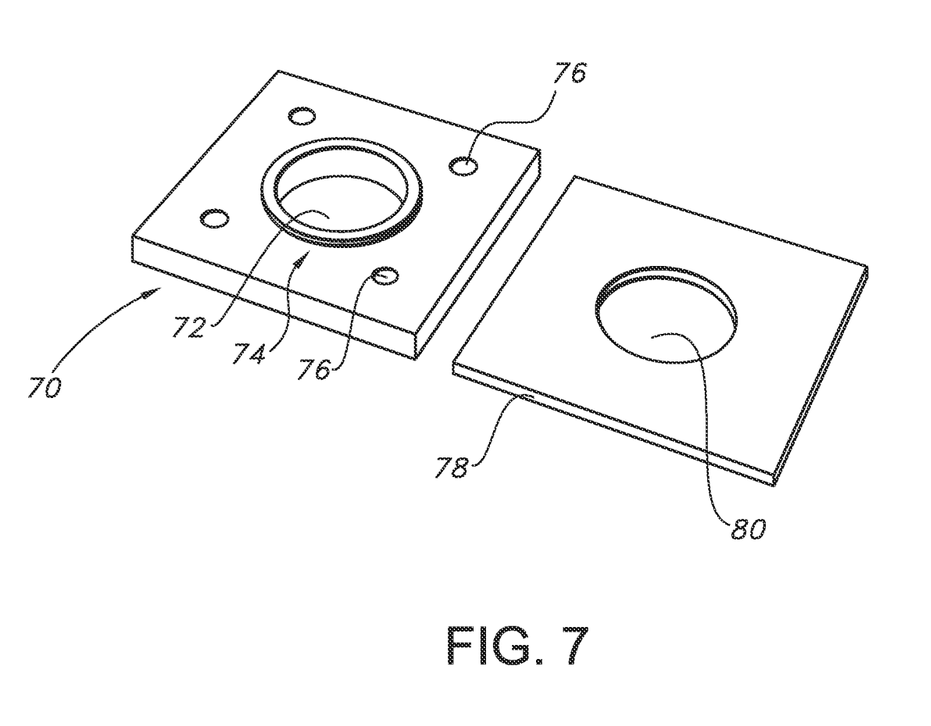
FIG. 7 is another embodiment of the gaskets used to form the tissue culture chip. In this embodiment, opening 72 in gasket 70 has a raised ridge 74 surround opening 72. Raised ridge 74 is matingly received by opening 80 of gasket 78 when gasket 70 and 78 are assembled to form the tissue culture cassette.
Figure 8:
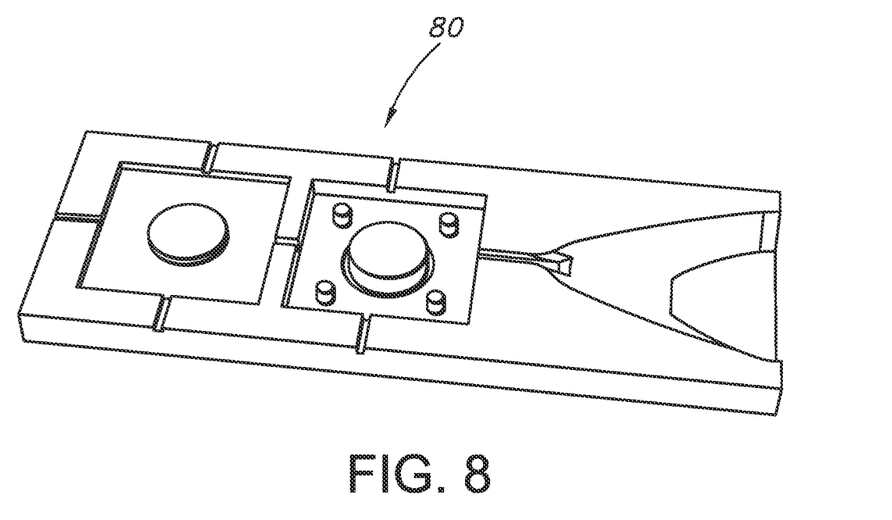
FIG. 8 is an exemplary mold 80 used to produce the gaskets for the tissue culture chip.
Figure 9:
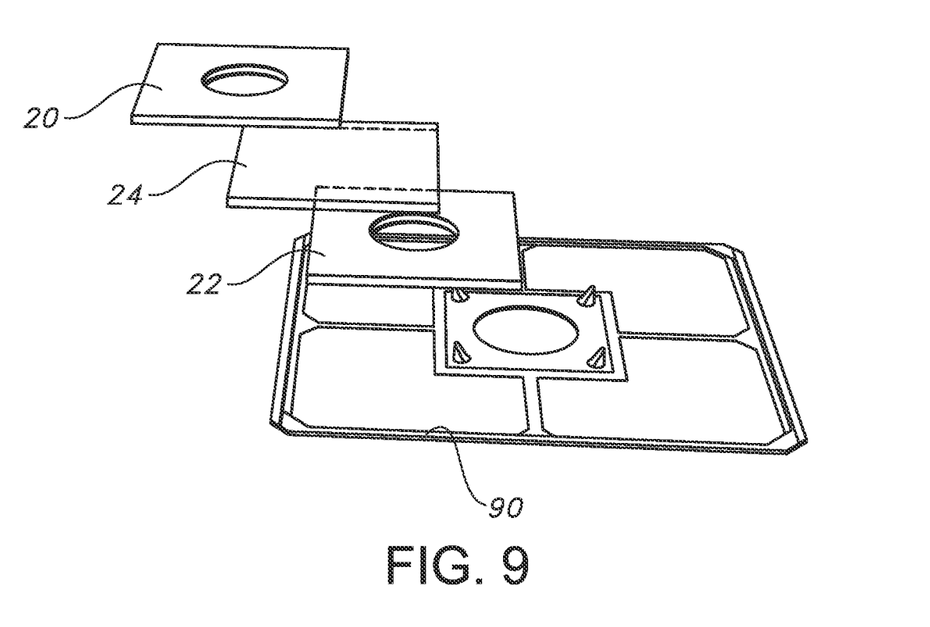
FIG. 9 is an exploded view of an exemplary tissue culture chip and tissue chip holder 90.
Figure 10:
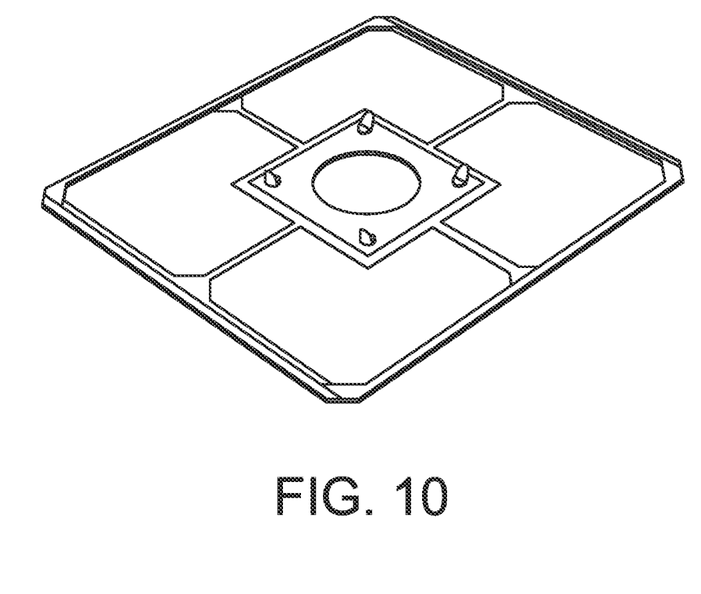
FIG. 10 is a tissue chip holder that stabilizes the flat chip of graft/matrix so it stays positioned over the openings.
Figure 11A:
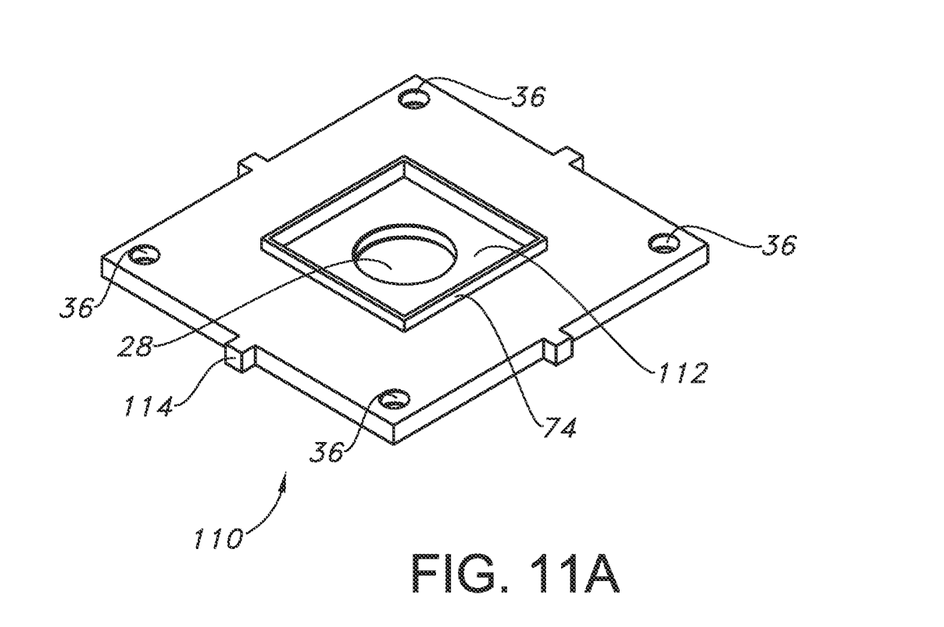
FIG. 11A shows gasket 110 that has a raised, square ridge 74 around opening 28 to form a reservoir 111
Figure 11B:
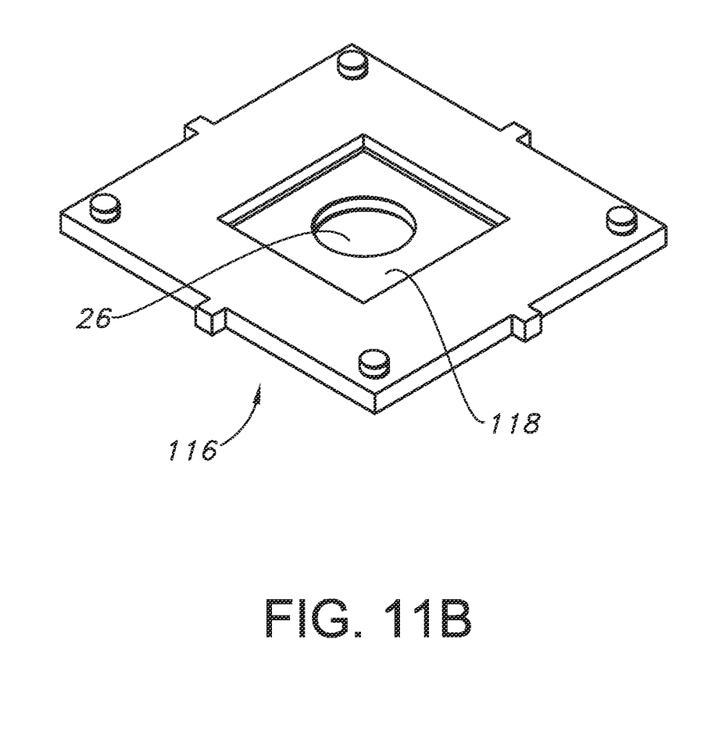
FIG. 11B shows gasket 116 that has a square shaped recession 118 that matingly receives raised ridge 74 of gasket 110.

Exemplary tissue chips include a tissue culture matrix or scaffold mounted on a frame made of two gaskets. FIGS. 2A-C show the components of an exemplary tissue chip. FIGS. 5 and 9 show an exploded views of tissue culture cassette or tissue culture chip. FIGS. 7 and 11A-11B show embodiments of gaskets used to form a tissue culture cassette.

1. Matrices and Scaffolds

The tissue culture matrix or scaffold 24 is preferably an acellularized tissue, such as acellularized tissue such as acellularized trachea or other material that form an impermeable barrier between the two media reservoirs. Cell culture matrices and scaffolds are known in the art and can be made of biodegradable, natural, or synthetic material. Scaffolds are typically artificial structures capable of supporting three-dimensional tissue formation. Other suitable cell culture matrices or scaffolds include, but are not limited to MATRIGEL®, collagen, polylactic acid, polyglycolic acid (PGA), and polycaprolactone (PCL).

Natural materials for producing suitable matrices and scaffolds include, but are not limited to extracellular matrix material, fibrin, and polysaccharidic materials, such as chitosan or glycosaminoglycans (GAGs). GAGs such as hyaluronic acid, possibly in combination with cross linking agents (e.g. glutaraldehyde, water soluble carbodiimide, etc. . . . ) can be used as a scaffold material. Functionalized groups of scaffolds may be useful in the delivery of small molecules (drugs) to specific tissues.

Additional materials suitable for use as scaffolds are found in Carletti E, Motta A, Migliaresi C., *Methods Mol Biol.;* 695:17-39 (2011) which is incorporated by reference in its entirety.

2. Gaskets

The gaskets 20, 22, 70, 78, 110, and 118 can be made of any biocompatible material. Preferably, the material is compressible so that a mechanical seal between the tissue chip and the media reservoirs can be made to prevent media leakage. Suitable materials include, but are not limited to silicone and silicone blends such as polyvinyl siloxane. Other materials that can be used include polytactic acid or materials useful for production of the gasket by injection molding.

As shown in FIG. 5, gaskets 20 and 22 contain openings 26 and 28. Matrix or scaffold 24 is placed between gaskets 20 and 22 and projections 34 of gasket 20 are inserted into openings 36 of gasket 22 to great a tissue chip 18. Openings 26 and 28 of the gaskets are aligned with openings 16 of the media reservoirs 12 to form a single opening that allows media from reservoirs 12 to bathe top and bottom sides of matrix or scaffold 24. Projections 34 and openings 36 can be any geometric shape including, but not limited to circular, square, oval, diamond, rectangular, or combinations thereof.

FIGS. 7 and 11A-11B show another embodiment of the gaskets that can be used to form the tissue chip or tissue culture cassette. An important feature of this embodiment is raised ridge 74. In FIG. 7, ridge 74 is circular. In FIG. 11B raised ridge 74 is square. In FIG. 7, ridge 74 is matingly received by opening 80. In FIG. 11B, gasket 116 has a recession or reservoir 118 that receives ridge 74 when the gaskets are combined. The embodiment shown in FIGS. 11A-11B shows a tissue chip that has a reservoir 118 for the matrix or scaffold 24 when the gaskets are assembled. The matrix or scaffold 24 typically fills reservoir 118 and covers opening 26, 3. Representative Tissue Chip FIG. 5 shows an exemplary tissue chip 18 in which gasket 20 contains projections 34 that are matingly received into openings 36 within gasket 22 to form the tissue chip 18. Matrix or scaffold 24 can be cut to have the same length and width of gasket 20 to cover opening 26 and optionally projections 34. In another embodiment, holes can be cut into the matrix or scaffold 24 to allow projections 34 to fit securely through matrix or scaffold 24 and into openings 36 of gasket 22. When gaskets 20 and 22 are combined so that projections 34 are inserted into openings 36, the gaskets sandwich the tissue chip on both sides and create a water-tight seal, thus allowing separation of the two media reservoirs 12 shown in FIG. 4. Methods of securing matrix or scaffold 24 between the gaskets include using mechanical pressure, physical stabilization via sharp projections that pierce the matrix, fibrin glue, cyanoacrylate (super-glue) or octoacrylate (DERMABOND®) glue, suture, or any variety of suitable securing material.

D. Receiver Block

Figure 3A:
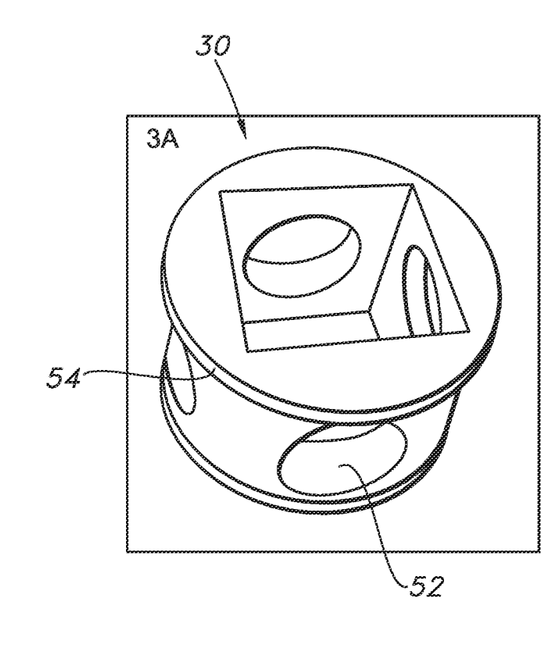
FIG. 3A shows an exemplary receiver block 30.

The media reservoirs 12 are held together with sufficient force to produce a mechanical seal between the reservoirs and the tissue chip. In a preferred embodiment, the media reservoirs are held together using a receiver block 30. An exemplary receiver block 30 is cylindrical on the outer surface (to fit within the rolling-flask bioreactor assembly described in U.S. Ser. No. 61/794,938) (FIG. 3A). There are also observation ports 52 on each side, allowing direct monitoring and visualization of the tissue chip throughout the incubation process. One embodiment incorporates real-time monitoring, where the tissue chip or media can be queried without removal from the bioreactor. These queries could include: microscopy+/−fluorescence to evaluate cell migration and ingrowth; laser interefereometry to measure pH, turbidity of the media, cell viability counts, and others.

Figure 3B:
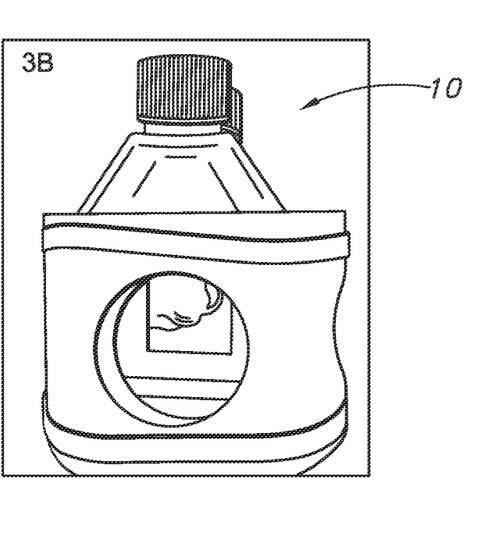
FIG. 3B shows a top view of an exemplary bioreactor 10.

The compression of the media reservoirs by the receiver block can be increased, for example by using elastomeric bands 54 or hose clamps (FIG. 3B).

Figure 4:
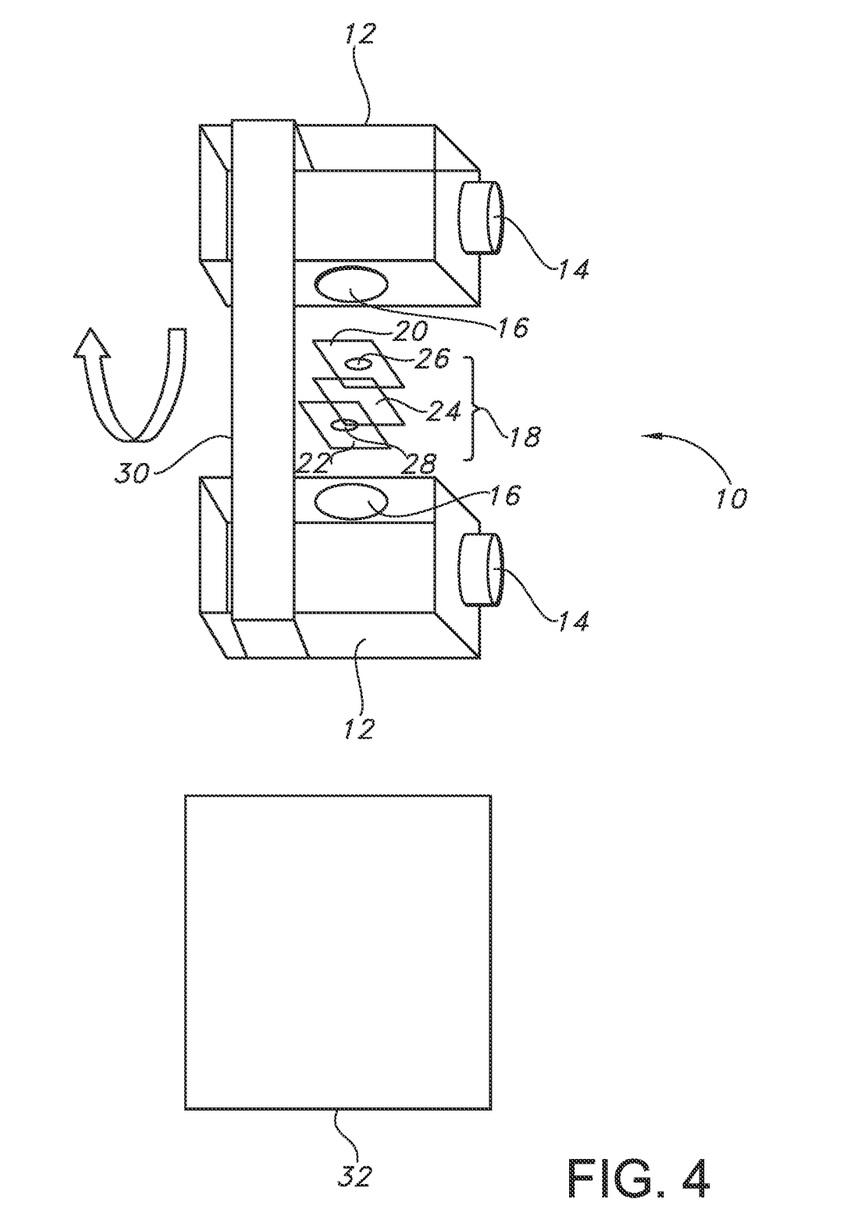
FIG. 4 shows an exploded view of a representative dual chamber rotary bioreactor.

In one embodiment, the media reservoirs 12 are held together with a band, belt, cord, cable 30 that compresses the reservoirs to form a water tight seal to inhibit or reduce leakage of media into the environment. Band 30 can be elastomeric or adjustable, E. Exemplary Rotary Bioreactors FIG. 4 shows an exemplary dual chamber bioreactor 10 that bathes a cell culture matrix or scaffold 26 in a constantly changing air-liquid interface to maximize nutrient, oxygen, and waste product exchange between cells in or on the scaffold 24 with the media on a top and bottom side of the scaffold 24. The bioreactor 10 contains media reservoirs 12 that can contain the same or different media allowing growth of distinct cell populations for multi-layered thick tissue engineering. This configuration is distinct from other current tissue bioreactors that only produce micron-thick tissues. Media and cells can be added or removed through ports 14.

The media reservoirs 12 contain at least one opening 16. The openings in each reservoir are aligned to form an opening between the two reservoirs that is covered by the tissue chip 18. Tissue chip 18 contains gaskets 20 and 22 separated by matrix or scaffold 24. The tissue culture matrix or scaffold 24 is attached to the one of the gaskets 20 and covers opening 26. Gasket 22 has a similar opening 28. When the gaskets are combined with the matrix or scaffold they form a tissue chip 18 that functions as a diffusion barrier between the two media reservoirs. Openings 26 and 28 in gaskets 20 and 22 align with each other and align with opening 16 in media reservoirs 12 so that the scaffold is exposed to media from both reservoirs 12. The media reservoirs are compressed together by a clamp or receiver block 30.

The assembled bioreactor 10 as shown in FIG. 3B is then connected to a motor 32 that rotates the bioreactor around the horizontal axis. The motor 32 can be a tumbler and is described in U.S. Ser. No. 61/794,938 which is incorporated by reference in its entirety.

II. Methods of Use

A. Single Experiment Tissue Engineering

The disclosed rotating bioreactors enable growth of complex (multi-layered) tissue for instance epithelial and chondrocyte, or bladder with epithelium and fibroblasts, or gut with epithelium and serosa) without requiring production of an entire organ. Experimental conditions (cytokines, length of incubation, etc) can be manipulated and measured white minimizing the amount of starting material needed.

A first population of cells is seeded on one side of an assembled tissue chip. The cells are allowed to adhere to matrix and scaffold. Once the cells adhere, the tissue chip is flipped and a second population of cells is seeded on the second side of the tissue chip. The cells are allowed to adhere. The loaded tissue chip is combined with the two media reservoirs and the receiver block to produce the assembled bioreactor as shown in FIG. 3B. Media is added to each reservoir and the bioreactor is placed on a tumbler to rotate the bioreactor. The rotation of the bioreactor exposes the cells periodically to media and shear forces. The rotation of the bioreactor can be adjusted to optimize tissue growth in the bioreactor.

B. Skin Graft Production

Current tissue engineered skin replacements for clinical use are micron-scale, single-cell thickness tissue sheets. These are living keratinocytes but are extremely fragile and the durability after in vivo application has been questioned. Other non-living products (e.g., ALLODERM®) are decellularized dermis only, and must be repopulated in-vivo. There is evidence (from tracheal tissue engineering) that multilayered grafts result in more durable tissue constructs than single-layer (Go, Jungebluth, Baiguero, et al. J Thorac Cardiovasc Surg. 139:437-443). The disclosed bioreactors allow production of complex living tissue grafts, including epidermal (keratinocyte) and dermal (fibroblast, +/− blood vessels) components. These grafts would be thick (100 microns to 1 millimeter) and much more robust.

C. Dermatology Drug Testing

Skin sheets can be produced and used to measure effects of dermatologic products (and cosmetics) as an alternative to in vivo animal testing. Compounds of interest can be applied to the engineered skin to determine the effects, if any of the compounds on the engineered skin. For example, toxicity and mutagenicity of a test compound can be assessed by applying the compound to the engineered skin and observing for cell death or mutation.

D. Skin Cancer Testing

Skin sheets can be produced and used to model skin cancer as an alternative to early in vivo animal testing. Many potential chemotherapy small molecules look promising in cell culture, but fail on in vivo testing. The closest thing available currently is MATRIGEL® or similar technologies that allow growth of cancer cells in a 3-D manner within a proteoglycan hydrogel (such as collagen). While that is an improvement over growth in 2D on a tissue culture flask, the disclosed bioreactors if applied using decellularized tissue in particular, use scaffolds that retain the numerous cytokines and growth factors embedded in the natural extracellular matrix. It is even possible that the dual media chamber design could allow growth of very complex tissue microenvironments including stem cells, fibroblasts, and/or immune effector cells to create extremely realistic and predictive pre-clinical laboratory models.

One embodiment provides culturing skin cells obtained from a human subject having or suspected of having skin cancer to produce an engineered skin sheet containing skin cancer cells, applying anti-cancer compounds to the engineered skin, and selecting the anti-cancer compound that kills the skin cancer cells in the engineered skin. The disclosed bioreactors allow the identification of the chemotherapeutic agents that are effective thereby avoiding the need to administer chemotherapeutic agents to patients that may be ineffective.

E. Mucosal Sheets

The skin sheets could be modified to produce mucosal sheets (for resurfacing of nasal defects, head and neck cancer resection defects, and other uses). In this embodiment, keratinocytes (epithelial cells) would be obtained from biopsy specimens, for example a buccal mucosa, inferior turbinate or bronchial biopsy. These keratinocytes would be separated as commonly performed (Liu and Karasek, J Inv Derm 71:(57-64) by mechanical and enzymatic disruption of the biopsy specimen to yield individual cells. These cells would be applied to one surface of the cell culture matrix. In a preferred embodiment, this matrix would consist of decellularized (cadaveric) mucosal tissue of the appropriate anatomic site. The opposite side of the matrix would be seeded by support cells of a different derivation, in a preferred embodiment these would be fibroblasts. In the preferred embodiment these fibroblasts are autologous (from the same individual or animal), or allogenic (from the same species but a different individual) cells may also be used. In the preferred embodiment fibroblasts are cultured from tissue biopsies such as dermal biopsy, or derived from progenitor cells such as adipose derived stem cells. The two layers of cells are allowed to populate the matrix to produce a structure modeled after in-vivo mucosal structures, having thickness and resistance to mechanical shear orders of magnitude greater than single-cell thickness cell sheets lacking the support matrix and multiple cell types. In a preferred embodiment of the invention, these mucosal sheets could be used to line surgical sites such as to reconstruct a tracheal mucosal defect, or to reconstruct an oral, pharyngeal or nasal mucosal defect following head and neck cancer resection. These mucosal sheets would also be ideal for studying virus-mucosa interactions, which currently can be quite problematic. This capability would be very useful in studying respiratory viruses such as SARS or the newer MERS virus. The current invention (via the real-time monitoring ability) will allow identification of virus-epithelium attachment mechanisms, and development of specific inhibitors of this process and/or viral replication process.

F. Viral Particle Production

Epithelial-trophic viruses, such as human papillomavirus, SARS and MERS, can be quite difficult to produce in-vitro, Production of viral particles is often required for studying initial interactions, producing disease in animal models, etc. In the case of human papillomavirus, viral particle production in cell culture requires growth in a relatively undifferentiated (basal) keratinocyte layer, placed at an air-liquid interface. This is currently accomplished by floating a raft of such keratinocytes on a thin bed of cell culture media, and is technically demanding (McLaughlin-Drubin, Meyers. Methods Mol Med. 119:1711-86). Certain embodiments allow easier methods of viral particle production compared to the currently practiced organotypic raft culture method. In this embodiment, keratinocytes (either primary or cultured immortal keratinocytes) would be seeded onto a matrix. In a preferred embodiment, this matrix would be manufactured using a biocompatible fiber-based mesh such as from electrospun polycapronolactone fibers. By creating an air-liquid interface while also producing constant media exchange (by the rotation of the construct), the disclosed bioreactor has the potential to support high-volume virus production.

G. High-Throughput Screening

An extension of each of the above embodiments would be to micro-scale and place multiple tissue-chips in an array, similar in concept to a 96-well plate. This would allow variation and replication of multiple experimental conditions in a high throughput manner. For example, current technology to support experimental discoveries and advances in multi-layered organ tissue engineering require either growing an entire organ for each condition or manipulation tested, or creating multiple, small thin-slice replicas which are placed in petri dish wells. The latter allows more high-throughput investigations compared to the whole-organ approach, but eliminates the possibility of two distinct fluid/conditions present in the dual-chambered bioreactor approach. Many multi-layered organs or tissues are reliant on distinct fluid conditions in the extraluminal versus intraluminal compartments, which the thin-slice approach does not allow. In the present disclosure, high throughput assays can be performed while maintaining the ability to manipulate two distinct fluid compartments. Thus, the tissue chip would contain 10 to 100 openings. Each opening would be covered with cell culture matrix or scaffolding. Each opening can be treated with a different test compound. In one embodiment, each chamber (two per opening and associated scaffolding) could be individually manipulated via microfluidic channels. The entire tissue chip can then be cultured and observed for phenotypic changes in response to drug treatment.

EXAMPLE

Example 1: Decellularized Tracheal Tissue Presents an Effective Diffusion Barrier Diffusion cassettes were constructed from plastic spectrophotometry cuvettes, with a patch of decellularized tracheal tissue interposed between two holes in the sidewall of the cuvettes, Phosphate buffered saline with 70 kDa Dextran labeled with FITC was placed in the left cuvette, and PBS in the right. Imaging was performed after 24 hours at 37° C. Similar experiments were repeated with albumin, and IgG labeled with quantum nanocrystals.

As shown in FIG. 5, decellularized tracheal patches create an effective diffusion barrier to water, and several biological molecules such as albumin, dextran and IgG.

We claim:

1. A bioreactor comprising a first and second media reservoir, wherein the first and second media reservoir comprise at least one opening on a cell culture surface of the reservoir, wherein the first and second reservoirs are positioned so that the cell culture surfaces containing the opening of each reservoir face each other and the opening of each reservoir aligns with the opening of the other reservoir; and
   a tissue culture cassette comprising a first and second gasket, wherein the first and second gaskets each comprise an opening that aligns when the first and second gaskets are combined, and
   a cell culture matrix or scaffold sandwiched between the first and second gasket that covers the aligned openings of the gaskets to form an impermeable tissue culture cassette,
   wherein the tissue culture cassette is positioned between the first and second media reservoirs so that the covered openings in the first and second gaskets align with the openings in the cell culture surfaces of the first and second media reservoirs to form an impermeable barrier between the first and second media reservoirs; and
   a means for applying sufficient pressure on the media reservoirs to produce a seal between the media reservoirs and the tissue culture cassette to prevent media leakage out of the openings in the cell culture surface of the media reservoirs.

2. The bioreactor of claim 1, wherein the media reservoirs are standard tissue culture flasks modified to contain an opening in a cell culture surface of the tissue culture flask.

3. The bioreactor of claim 1, wherein the means for applying pressure is one or more clamps.

4. The bioreactor of claim 1, wherein the means for applying pressure is a receiver block.

5. The bioreactor of claim 4, wherein the receive block optionally includes elastomeric bands to increase the pressure.

6. The bioreactor of claim 4, wherein the receiver block comprises one or more observation portals for visual, microscopic, or electromagnetic observation of the media or cells in culture.

7. The bioreactor of claim 1, wherein the first gasket comprises projections that are matingly received by the second gasket to form the tissue culture cassette.

8. The bioreactor of claim 1, wherein the tissue culture matrix or scaffold comprises decellularized tissue.

9. The bioreactor of claim 1, wherein the gaskets comprise vinyl polysiloxane.

10. The bioreactor of claim 1, wherein the tissue culture cassette comprises a plurality of openings covered by the cell culture matrix or scaffold.

11. The bioreactor of claim 10, wherein the plurality of openings includes at least 10 to 100 openings.

12. The bioreactor of claim 1, wherein the tissue culture cassette is removable from the first and second media reservoirs.

13. A bioreactor comprising a first and second media reservoir, wherein the first and second media reservoir comprise at least one opening on a cell culture surface of the reservoir, wherein the first and second reservoirs are positioned so that the cell culture surfaces containing the opening of each reservoir face each other and the opening of each reservoir aligns with the opening of the other reservoir; and
   a tissue culture cassette comprising a first and second gasket, wherein the first and second gaskets each comprise an opening that aligns when the first and second gaskets are combined, and
   a cell culture matrix or scaffold sandwiched between the first and second gasket that covers the aligned openings of the gaskets to form an impermeable tissue culture cassette,
   wherein the tissue culture cassette is positioned between the first and second media reservoirs so that the covered openings in the first and second gaskets align with the openings in the cell culture surfaces of the first and second media reservoirs to form an impermeable barrier between the first and second media reservoirs; and
   a seal between the media reservoirs and the tissue culture cassette to prevent media leakage out of the openings in the cell culture surface of the media reservoirs.

14. The bioreactor of claim 13, wherein the tissue culture cassette is removable from the first and second media reservoirs.

15. The bioreactor of claim 13, wherein the media reservoirs are standard tissue culture flasks modified to contain an opening in a cell culture surface of the tissue culture flask.

16. The bioreactor of claim 13, wherein the seal comprises a sealant.

17. The bioreactor of claim 13, further comprising one or more clamps on the media reservoirs to produce the seal between the media reservoirs and the tissue culture cassette.

18. The bioreactor of claim 13, further comprising at least one receiver block on the media reservoirs to produce the seal between the media reservoirs and the tissue culture cassette.

19. The bioreactor of claim 18, wherein the receive block optionally includes elastomeric bands to increase the pressure.

20. The bioreactor of claim 18, wherein the receiver block comprises one or more observation portals for visual, microscopic, or electromagnetic observation of the media or cells in culture.

\* \* \* \* \*